United States Patent [19]

Cecco et al.

[11] Patent Number: 4,808,924
[45] Date of Patent: Feb. 28, 1989

[54] CIRCUMFERENTIALLY COMPENSATING EDDY CURRENT PROBE WITH ALTERNATELY POLARIZED TRANSMIT COILS AND RECEIVER COILS

[75] Inventors: Valentino S. Cecco; Richard McIlquham; F. Leonard Sharp, all of Deep River, Canada

[73] Assignee: Atomic Energy of Canada Limited, Ottawa, Canada

[21] Appl. No.: 16,752

[22] Filed: Feb. 19, 1987

[51] Int. Cl.[4] .................. G01N 27/90; G01R 33/12
[52] U.S. Cl. ......................... 324/220; 324/225; 324/232; 324/242
[58] Field of Search ................ 324/219–221, 324/225, 232, 242, 243

[56] References Cited

U.S. PATENT DOCUMENTS

| | | | |
|---|---|---|---|
| 2,124,579 | 7/1938 | Knerr et al. | 324/242 X |
| 2,746,012 | 5/1956 | Price | 324/242 |
| 3,166,710 | 1/1965 | Schmidt | 324/242 |
| 3,202,914 | 8/1965 | Deem et al. | 324/242 |
| 3,241,058 | 5/1966 | Quittner | 324/242 |
| 3,271,662 | 9/1966 | Quittner | 324/233 |
| 3,444,459 | 5/1969 | Prindle et al. | 324/242 |
| 3,952,315 | 4/1976 | Cecco | 324/220 |
| 4,079,312 | 3/1978 | Osborn et al. | 324/225 X |
| 4,083,002 | 4/1978 | Allport | 324/232 X |
| 4,608,534 | 8/1986 | Cecco et al. | 324/220 X |

FOREIGN PATENT DOCUMENTS 0065325 11/1982 European Pat. Off. ............ 324/220

Primary Examiner—Gerard R. Strecker
Attorney, Agent, or Firm—Yoshiharu Toyooka

[57] ABSTRACT

An eddy current probe capable of detecting defects independent of orientation, with complete circumferential coverage in tubes, tubes under support plates, etc., is disclosed. The probe employs multiple coils, operating in transmit-receive mode, in which alternate coils are electromagnetically polarized in opposite directions. The probe detects localized defects and eliminates concentric variations.

12 Claims, 4 Drawing Sheets

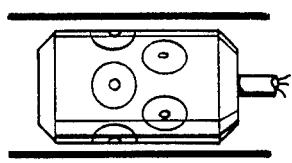
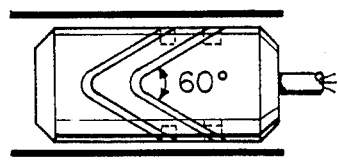
FIG. 1a
PRIOR ART
FIG. 1b
PRIOR ART
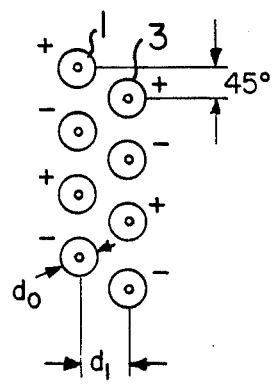
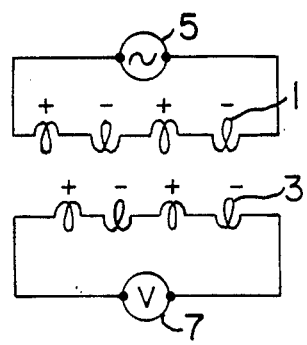
FIG. 2a
FIG. 2b
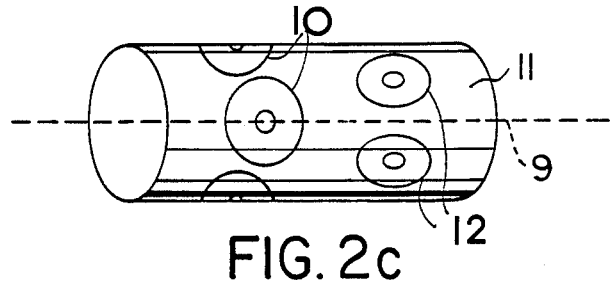
FIG. 2c

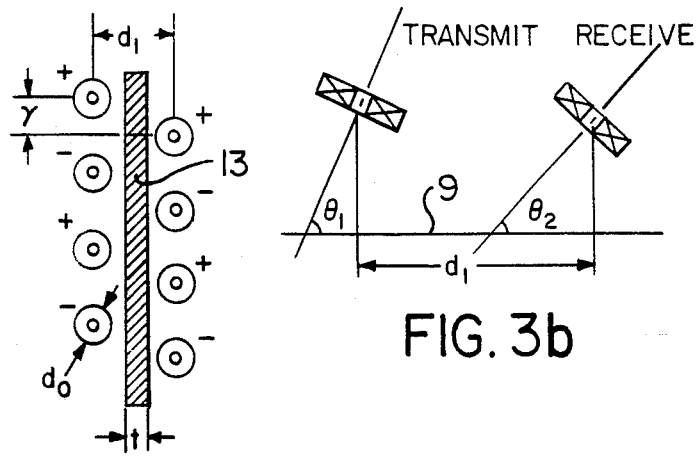
FIG. 3a
FIG. 3b
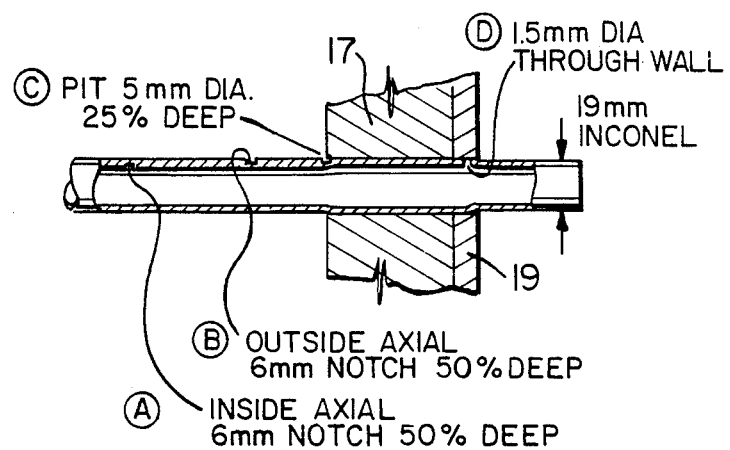
FIG. 4

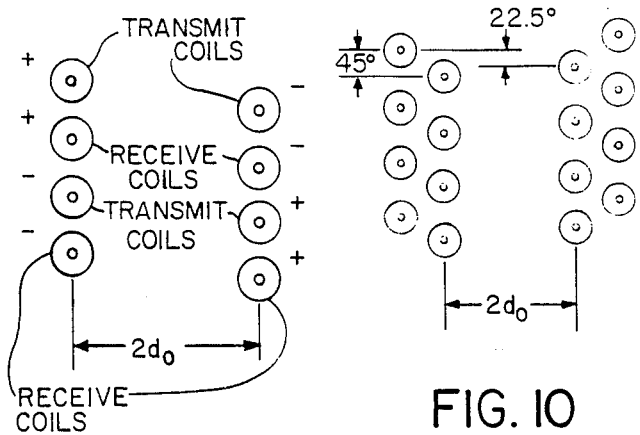
FIG. 9
FIG. 10
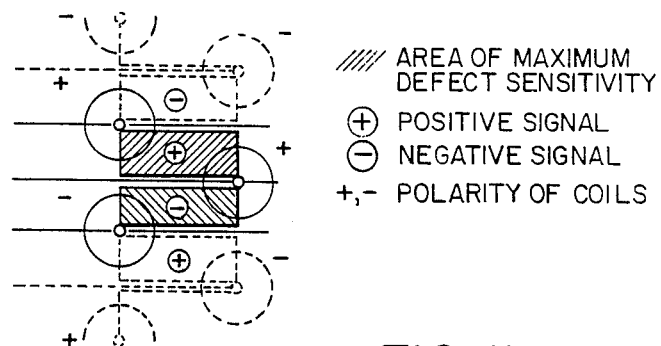
////  AREA OF MAXIMUM DEFECT SENSITIVITY
⊕   POSITIVE SIGNAL
⊖   NEGATIVE SIGNAL
+,− POLARITY OF COILS
FIG. 11

CIRCUMFERENTIALLY COMPENSATING EDDY CURRENT PROBE WITH ALTERNATELY POLARIZED TRANSMIT COILS AND RECEIVER COILS

This invention relates to the nondestructive testing of a tube made of an electrically conductive material and in particular to an eddy current probe having multiple transmit coils and receiver coils and capable of detecting, in a tube, both circumferential and axial cracks, fretting wear, shallow internal defects, etc. under ferromagnetic and non-ferromagnetic support plates. Therefore, in conventional eddy current probe, factors causing circumferential structural variations such as support plates, tubesheets, etc., positioned about a tube under inspection at locations along its length, changes in tube diameter, etc. introduce marked deviations in output signals, thus making the detection of defects very difficult if not impossible. In the present eddy current probes, however, these circumferentially variations are made invisible (compensated) in the output. Thus it is decided that, "Circumferentially compensating", "tubesheet compensating" or such terms are used to denote the ability throughout the present specification and claims.

BACKGROUND OF THE INVENTION

Eddy current testing is a non-destructive test technique based on inducing electrical currents in the material being inspected and observing the interaction between these currents and the material. Eddy currents are generated by electromagnetic coils in the test probe, and monitored simultaneously by measuring probe electrical impedance. Since it is an electromagnetic induction process, direct electrical contact with the sample is not required; however, the sample material must be electrically conductive.

When inspecting for defects, it is essential that flow of eddy currents be as perpendicular to defects as possible to obtain maximum response. If eddy currents flow parallel to a defect, there will be little distortion of the eddy currents and hence little change in probe impedance.

Various eddy current probes have been proposed for inspecting cylindrical or tubular components as seen in U.S. Pat. Nos. 3,952,315 Apr. 20, 1976 (Cecco), 4,079,312 Mar. 14, 1978 (Osborne et al.) and 4,083,002 Apr. 4, 1978 (Allport).

A conventional internal circumferential probe induces a flow of eddy currents parallel to the coil windings and therefore circumferential in direction. As mentioned above, coil impedance must change to sense a defect. This will occur only if eddy current flow path is disturbed. Circumferential defects parallel to this current, which present no significant area perpendicular to this path, will therefore not be sensed. Multiple coils in excitation coil assembly and in receiver coil assembly are also described in U.S. Pat. Nos. 3,241,058 Mar. 15, 1966 (Quittner) and 3,271,662 Sept. 6, 1966 (Quittner). The above two patents to Quittner teach sheet metal inspection using an odd number of coils with their axes perpendicular to test sample for transmit and an even number of coils for receiving. The transmit coils are electromagnetically polarized alternately but the receiver coils are polarized in same directions, thus enabling no circumferential or line compensation (a desired feature in the Quittner patent). They are very complex and sensitive to probe wobble. They also produce complicated output signals to analyze and are not readily applicable for cylindrical testing.

U.S. Pat. No. 3,444,459 May 13, 1969 (Prindle et al.) describes helical sensing coils slightly skewed relative to the axis of the tube. The coils are alternately polarized but must be in an elongated shape for 100% circumferential coverage and manageable axial probe length. The transmit coil is at least three times larger than the sensing coil coil assembly. The probe has no sensitivity to circumferential cracks.

It is a recognized problem that reliable detection and sizing of circumferential cracks, fretting wear, shallow internal defects etc. is made more difficult by the fact that they frequently occur in defect prone regions such as under tubesheets or support plates and in transition region of finned tubes. Heat exchangers and steam generator are normally assembled with tubes rolled into the tubesheet and then welded at the primary tubesheet face. Rolling is primarily performed to eliminate corrosion prone crevices. However, if tubes are rolled beyond the tubesheet secondary face they are prone to cracking.

The present invention makes use of multiple coils operating in the transmit-receive mode for detecting all localized defects, including circumferential cracks in a tube. The probes according to the present invention detect internally or externally any defects including defects under support plates. With a variety of coil configurations, a 100% circumferential coverage in single pass is possible with high defect sensitivity in the transition zone between expanded and unexpanded tubing.

OBJECTS OF THE PRESENT INVENTION

It is an object of the present invention to provide an eddy current probe which produces circumferentially compensated output signal.

It is a further object of the present invention to provide an eddy current probe which can detect defects (circumferential or non-circumferential) in a tube under tubesheet or support.

It is a still further object of the present invention to provide an eddy current probe which produces outputs similar in nature to those of conventional probes for ease of analyses.

SUMMARY OF THE INVENTION

Briefly stated, a circumferentially compensating eddy current probe according to the present invention includes a first pair of coil assemblies, the first and the second, the said first coil assembly having an even number of substantially identical first coils to be located adjacent to a tube under inspection and symmetrically about and in a first plane perpendicular to the central axis of the tube, the said first coils having axes which form an angle $\theta_1$ with the said central axis and being electromagnetically polarized alternately along their axes. The second coil assembly has the same even number of substantially identical second coils to be located adjacent to the tube under inspection and symmetrically about and in a second plane perpendicular to the central axis, the said second coils have axes which form an angle $\theta_2$ with the said central axis and being electromagnetically oriented alternately between two opposite directions along their axes. The said first and the said second coil assemblies are angularly displaced from each other about the said central axis to position each of the coils in one of the coil assemblies at midpoint of two adjacent coils in the other of the coil assembly. When energized, one of the coil assemblies generates magnetic fields in the tube in the said two opposite directions of the coils and the other coil assembly senses distortions in the magnetic fields and produces a circumferentially compensated output indicating essentially the presence of localized flaws in the tube.

BRIEF DESCRIPTION OF THE DRAWINGS

For a more complete understanding of the present invention and for further objects and advantages thereof, references may be made to the following description taken in conjunction with the accompanying drawings in which:

FIGS. 1(a) and 1(b) illustrate perspective views of the two prior art devices sensitive to circumferential cracks but without circumferential compenstion.

FIGS. 2(a), 2(b) and 2(c) show the coil configuration and electrical connection according to one embodiment of the invention.

FIGS. 3(a) and 3(b) are generalized planar views of the present invention indicating symbols for various parameters.

FIG. 4 is a steam generator tube mock-up used for testing of the probes of the present invention.

FIGS. 9 and 10 are simplified planar views showing coil configurations of two sets of coil assemblies according to two of the embodiments of the present invention for complete circumferential coverage.

FIG. 11 is a simplified view to be used for description of operation of the probe according to the invention.

DETAILED DESCRIPTION OF PREFERRED EMBODIMENT

Figure 5:
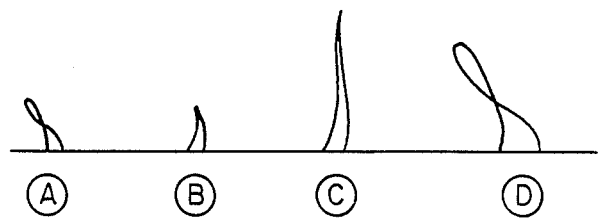
FIG. 5 shows output signals obtained in a test conducted on the mock-up of FIG. 4.

To detect circumferential defects the coil must induce currents at an angle to the cracks. FIGS. 1(a) and 1(b) show two possible types of tube probes. Neither has separate excitation and receiver coil assemblies. The probe in FIG. 1(a) induces currents in a circular pattern whereas the probe in FIG. 1(b) induces currents to follow the 30° coil angle. Both probes are of differential type in that the coils are electrically connected to generate differential signals using an ac bridge. While pancake type surface probes (single or multiple) have good sensitivity to surface cracks, they have low sensitivity to external defects, large lift-off noise, partial circumferential coverage and yield complex signals. In addition, the complex mechanical design required to minimize lift-off noise makes the probe prone to failure.

For detecting cracks under tubesheets and in transition regions of finned tubes etc, dual or multi-frequency eddy current methods are known. High test frequencies are very sensitive to tube expansion, low test frequencies are very sensitive to tubesheet and support plates, while intermediate ones are sensitive to defects, support plates and expansions. A proper mix of these multifrequency signals results in sensitivity primarily to defects.

Tubesheet compensating probes, according to the present invention are designed to simplify eddy current testing. Defects close to or under a tubesheet or support plates can be detected without using multifrequency compensating (mixing of signals) or small surface probes of the present invention. These probes, operating on conventional transmit-receive eddy current instruments, have built-in circumferential compensation such that support plates, tubesheets and expanded sections are virtually invisible. A complete tube inspection yields signals only from defects. They can be used to detect stress-corrosion cracks, short circumferential cracks, pits even in the presence of uniform copper deposits, and fretting wear under support plates. Inconel (Trade Mark) steam generator tubes, brass condenser tubes and copper, finned air conditioner heat exchanger tubes can be inspected with a single scan using a single frequency transmit-receive eddy current instrument.

FIGS. 2(a), 2(b), 2(c) show schematically configuration, location, and electrical connection of coils used in the first coil assembly and the second coil assembly, according to one preferred embodiment of the present invention. The coils can be disc-shaped electromagnetic coil of a so called pancake shape or can be of any shape depending upon the needs and structures desired.

Referring to the drawings, FIG. 2(a) shows circumferential coil configuration in a planar expression. Four substantially identical first coils in the first coil assembly 1 are shown in one row 90° apart in a circle. Four substantially identical second coils in the second coil assembly 3 are displaced axially by a distance $d_1$ from the first coil assembly and further rotated by 45° so that they are positioned at midpoints of two adjacent excitation coils. The diameter of the coils is designated by $d_0$.

Referring to FIG. 2(c), the probe housing is designated by 11 and the four first coils 10 are located circumferentially in the cross-sectional plane of the probe housing having an axis which is substantially coincidential with the center axis 9 of the tube under inspection. The second coils 12 are positioned circumferentially at midpoints of two adjacent first coils.

FIG. 2(b) shows electrical connections of the coils to an ac power supply 5 and an instrument 7 which measures a voltage generated in the second coil assembly 3.

In these figures and figures which will follow, the signs + and − indicate the polarities of the coils which can be chosen by either the direction of coil windings or by electrical connections among the coils. Therefore instead of configuration shown in FIG. 2(b) where coils are wound in opposite directions to each other, electrical connections can be altered to produce the same effect by still maintaining the serial nature of connections. It should also be noted that but the law of reciprocity, the probe functions similarly if an ac power supply is connected to the second coil assembly and the voltage measurement instrument to the first coils assembly.

The first coils are arranged in a first plane which coincides with the cross-sectional plane of the probes housing as shown in FIG. 2(c) and is perpendicular to the central axis of the tube. Like the first coils, the second coils are also arranged in a second plane perpendicular to the central axis of the tube. Typical values in this embodiment are $d_0$ (diameter of the coils)=5 mm, $d_1$ (distance between the coil assemblies)=5 mm and the diameter of the tube is 12.7 mm.

The distance $d_1$ can be varied to optimize the performance depending upon the type of material, size, etc. of the tube. For certain applications, the distance $d_1$ can be zero. A certain conductive material can be inserted as a partial shield in the space e.g. copper in order to shift the phase of the output signal.

A variety of coil configurations are possible and will be discussed in general terms below by referring to FIGS. 3(a) and 3(b).

In FIG. 3(a), a four coil arrangement in a coil assembly is shown. Several symbols are included to indicate certain variable parameters, e.g. $d_1$ the distance between the coil assemblies, that is, between two perpendicular planes, $d_0$ the diameter of coils, $\gamma$ the angular displacement of the two coils assemblies and t the thickness of a partial shield designated by 13. FIG. 3(b) shows a first coil and a second coil relative to the central axis 9 and spaced apart by the distance $d_1$. In the figure the angles of the first coil axis and the second coil axis formed with the central axis are designated by $\theta_1$ and $\theta_2$ respectively.

These parameters, $d_0$, $d_1$, $\gamma$, t, $\theta_1$, $\theta_2$ are variables and can be chosen to optimize the performance to suit the requirements. The number of coils in a coil assembly can also be chosen among even numbers and the said number determines $\gamma$, the angular displacement.

For each of the coil numbers $2(\gamma=90°)$, $4(\gamma=45°)$, $6(\gamma=30°)$ . . . , the following coil configurations are possible.

(1) $\theta_1=90°$, 270° alternating; $\theta_2=90°$, 270° alternating; $d_1=0$
(2) $\theta_1=90°$, 270° alternating; $\theta_2=0°$, 180° alternating; $d_1=0$
(3) $\theta_1=0°$, 180° alternating; $\theta_2=0°$, 180° alternating; $d_1=0$
(4) $\theta_1=90°$, 270° alternating; $\theta_2 90°$, 270° alternating; $d_1 \geq d_0$
(5) $\theta_1=90°$, 270° alternating; $\theta_2=0°$, 180° alternating; $d_1 \geq d_0$
(6) $\theta_1=0°$, 270° alternating; $\theta_2=0°$, 180° alternating; d, $\geq d_0$
(7) $\theta_1=90°$, 270° alternating; $\theta_2=90°$, 270° alternating; $d_1 \geq d_0+t$, $t \approx \delta$
(8) $\theta_1=90°$, 270° alternating; $\theta°=0°$, 180° alternating; $d_1 \geq d_0+t$, $t \approx \delta$
(9) $\theta_1=0°$, 180° alternating; $\theta_2=0°$, 180° alternating; $d_1 \geq d_0+t$, $t \approx \delta$
(10) $\theta_1=90°$, 270° alternating; $\theta_2 \approx 30°-60°$, 210°-240° alternating, $d_1 \geq 2d_0$
(11) $\theta_1=0°$, 180° alternating; $\theta_2 \approx 30°-60°$, 210°-240° alternating; $d_1 \geq 2d_0$.

In the above listing, $\delta$ is the standard depth of penetrating of a generated magnetic field by $$\delta = 50 \sqrt{\frac{\rho}{\mu_r f}},$$

where f is the test frequency, $\rho$ is electrical resistivity and $\mu_r$ is the magnetic permeability of the partial shield.

As can be understood readily, the configuration shown in FIGS. 2(a) and 2(c) comes under case No. 4 above with the number of coils being 4.

FIGS. 4 and 5 show a steam generator tube mock-up having various types of defects and output signals obtained by a probe constructed according to the present invention. In FIG. 4, the tube made of Inconel (Trade Mark) is shown to have a diameter of 19 mm. Various defects are shown at locations A, B, C and D. The tubesheet 17 is carbon steel and an Inconel (Trade Mark) overlay is at 19.

FIG. 5 illustrates output signals in X-Y impedance pattern obtained at locations A, B, C and D. The through-wall hole and 25% deep, 5 mm diameter external pit are readily detectable at the tubesheet expansion transition. The undistorted signals permit accurate defect sizing. The signals from the carbon steel tubesheet, Inconel (Trade Mark) overlay and tubesheet expansion are negligible.

Figures 6, 7, 8:
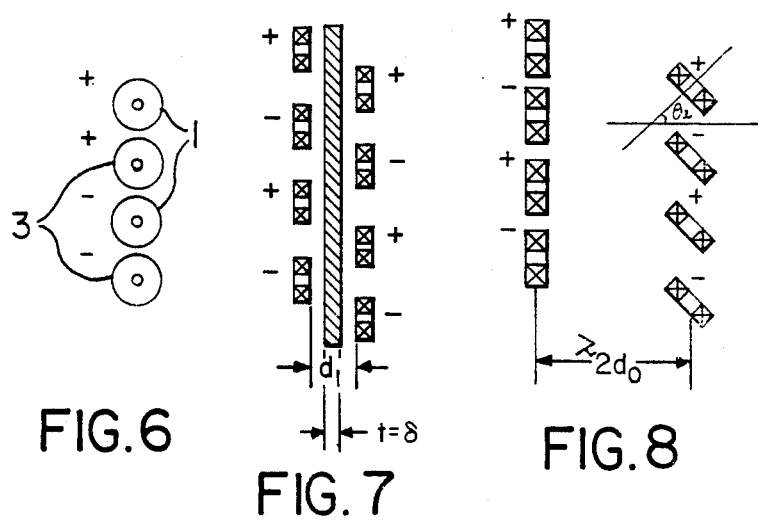
FIGS. 6, 7 and 8 are simplified planar views of some preferred embodiments of the present invention.

To aid in visualization of certain coil configurations listed above, references may be made to FIGS. 6, 7 and 8.

In FIG. 6, an embodiment under coil configuration Case No. 1, is shown in that 2 coils are provided in each of coil assemblies 1 and 3. $\theta_1$ and $\theta_2$ are each alternated between 90° and 270°. The coil assemblies are interchangeable in that the first coil assembly can be transmitting and the second coil assembly receiving or vice versa with similar results.

FIG. 7 shows all the coils (the first coils and the second coils) being axially aligned but alternately polarized, thus $\theta_1$ and $\theta_2$ and each chosen to be alternately 0° or 180°. A partial shield of a thin copper having a thickness equal to $\delta$ is provided as a phase shifter of the output defect signal relative to probe wobble signal. As in the case of FIG. 6, the coil assemblies are interchangeable as to transmit and reception functions.

FIG. 8 shows still another embodiment which comes under case No. 11. This embodiment minimizes direct coupling of the first (transmit) and the second (receive) coil assemblies but maximizes sensitivity to external defects. The embodiment further minimizes probe wobble signal and also distorts localized defect signals so that they become more distinguishable from the probe wobble noise.

As can be easily visualized, all the coil configurations can be implemented by an internal probe as well as by and external probe in that the coils can be positioned on one side of the tube inside or outside. With no changes in characteristics.

All the coil configurations so far discussed leave certain areas of circumference undetected, e.g. small areas that pass right under the centers of the coils. However a 100% circumferential coverage can be attained by providing a second set of coil assemblies identical to the first set but slightly displaced angularly therefrom.

Therefore for all the possible configurations listed above, the first and the second sets of coil assemblies are spaced axially apart angularly from each other by $\frac{1}{2}\gamma$. ($\gamma$ being angular displacement between first and the second coils in each set.)

FIGS. 9 and 10 show two of the said possible configurations as examples.

Referring to FIG. 11, the operation of the present invention will be briefly explained. As an example, the embodiment shown in FIG. 3(a) is considered. All other embodiments can be similarly analyzed. In FIG. 11, two transmit coils and one receive coil are shown in real line. The transmit coils connected with alternating N-S, S-N polarities result in:

Magnetic field bulging from one coil to the other, inducing eddy currents under and between the coils;

Magnetic flux being reasonably uniform at inner and outer tube surfaces; and

Magnetic field inducing eddy currents to flow at an angle to the tube axis at the indicated area of maximum sensitivity. This allows detection of axial and circumferential cracks.

The receive coils connected with alternating N-S, S-N polarities result in:

High defect sensitivity areas between transmit and receive coils;

Each adjacent area having alternative positive and negative sensitivity. For four transmit coils and four receive coils, there are four positive and four negative defect sensitivity areas;

These alternating defect sensitivities around the tube circumference resulting in cancellation of signals from symmetrical (concentric) variations, such as support plates, tubesheet and expansion areas. Output signals are produced only from localized defects.

Resultant signal from localized defects is similar to conventional bobbin probes, thus facilitating signal analyses. This allows defect sizing even under support plates or tube expansion regions.

We claim:

1. A circumferentially compensating eddy current probe for detecting localized flaws in a tube having a central axis and made of an electrically conductive material, while compensating for circumferential structural variations therein, comprising
   a first coil assembly and second coil assembly;
   the said first coil assembly having an even number of substantially identical first coils to be located adjacent to the tube under inspection and symmetrically about and in a first plane perpendicular to the central axis, the said first coils having axes which form an angle $\theta_1$, with the said central axis and alternate first coils being electromagnetically polarized in two opposite directions along their axes;
   transmitter energizing means coupled to said first coil assembly for energizing the said first coil assembly;
   the said second coil assembly having the same even number of substantially identical second coils to be located adjacent to the tube under inspection and symmetrically about and in a second plane perpendicular to the central axis, the said second coils having axes which form an angle $\theta_2$ with the said central axis and alternate second coils being electromagnetically polarized in two opposite directions along their axes; and
   receiver sensing means coupled to said second coil assembly for sensing current generated in the said second coil assembly;
   the said first coil assembly and the said second coil assembly being angularly displaced from each other about the said axis to position each of the coils in one of the coil assemblies at midpoint of two adjacent coils in the other of the coil assemblies;
   so that when energized, the said first coil assembly generates magnetic fields in the tube in the said two opposite directions of the coils and the said second coil assembly senses distortions in the magnetic fields and produces a circumferentially compensated output indicating essentially the presence of localized flaws in the tube.

2. The eddy current probe according to claim 1 wherein:
   the angles $\theta_1$ and $\theta_2$ are each selected from a group of angles consisting of 0° and 90°.

3. The eddy current probe according to claim 1 wherein:
   the angle $\theta_1$ is selected from a group consisting of 0° and 90°; and
   the angle $\theta_2$ is an angle between approximately 30° and 60°.

4. The eddy current probe according to claim 2 wherein:
   the said first and the said second planes are axially spaced from each other by a predetermined distance $d_1$ selected from a group of distances expressed by $d_1 = 0$ and $d_1 \geq d_0$ where $d_0$ is the diameter of the larger of the first coils and the second coils.

5. The eddy current probe according to claim 2 wherein:
   the said first and the said second planes are axially spaced from each other by a predetermined distance $d_1$, and partial magnetic shield means of a thickness t is provided therebetween, the distance $d_1 \geq d_0 + t$ where $d_0$ is the diameter of the larger of the first coils and the second coils and t is substantially equal to the standard depth of penetration $\delta$ of the generated magnetic fields.

6. The eddy current probe according to claim 3 wherein:
   the said first and the said second planes are axially spaced from each other by a predetermined distance $d_1$ expressed by $d_1 \geq 2\ d_0$, where $d_0$ is the diameter of the larger of the first and the second coils.

7. The eddy current probe according to claim 4 wherein:
   the said even number of the first and the second coils is a number selected from a group consisting of 2, 4, and 6; and
   the first and the second coil assemblies are provided on a probe housing to be freely movable along the central axis inside the tube.

8. The eddy current probe according to claim 5 wherein:
   the said even number of the first and the second coils is a number selected from a group consisting of 2, 4, and 6; and
   the first and the second coil assemblies are provided on a probe housing to be freely movable along the central axis inside the tube.

9. The eddy current probe according to claim 6 wherein:
   the said even number of the first and the second coils is a number selected from a group consisting of 2, 4, and 6; and
   the first and the second coil assemblies are provided on a probe housing to be freely movable along the central axis inside the tube.

10. The eddy current probe according to claim 7 further comprising:
    a second pair of coil assemblies including third and fourth coil assemblies;
    the said second pair being identical to the first pair but spaced axially therefrom by a distance $d_1$ greater than 2 $d_0$ and rotated about the central axis with respect to the first pair.

11. The eddy current probe according to claim 8 further comprising:
    a second pair of coil assemblies including third and fourth coil assemblies;
    the said second pair being identical to the first pair but spaced axially therefrom by a distance $d_1$ greater than 2 $d_0$ and rotated about the central axis with respect to the first pair.

12. The eddy current probe according to claim 9 further comprising:
    a second pair of coil assemblies including third and fourth coil assemblies;
    the said second pair being identical to the first pair but spaced axially therefrom by a distance $d_1$ greater than 2 $d_0$ and rotated about the central axis with respect to the first pair.

* * * * *